United States Patent [19]

Gigliello

[11] 3,981,804
[45] Sept. 21, 1976

[54] APPARATUS FOR SEPARATING MULTIPHASE FLUIDS

[75] Inventor: Joseph F. Gigliello, Corning, N.Y.

[73] Assignee: Corning Glass Works, Corning, N.Y.

[22] Filed: June 25, 1975

[21] Appl. No.: 590,127

[52] U.S. Cl. ............................ 210/516; 210/DIG. 23
[51] Int. Cl.$^2$ .................................... B01D 21/26
[58] Field of Search .............. 23/230 B, 258.5, 259, 23/292; 128/2 F, 214 R, 218 M, 272.1, DIG. 5, DIG. 28; 206/219, 221, 222; 215/DIG. 8; 210/83, 84, 514–518, DIG. 23, DIG. 24; 233/1 A, 1 R, 26

[56] References Cited
UNITED STATES PATENTS 3,920,549    11/1975    Gigliello et al. ............. 210/DIG. 23

Primary Examiner—John Adee
Assistant Examiner—Robert G. Mukai
Attorney, Agent, or Firm—Thomas J. McNaughton; Burton R. Turner; Clarence R. Patty, Jr.

[57] ABSTRACT

In combination with an apparatus for centrifugally separating and partitioning differing-density phases of a multiphase fluid including a container and gel-like means initially positioned within an end portion of the container for forming a partition between the differing-density phases, the improvement comprising flow control means initially partially submerged in the gel-like means for directing the flow of the gel-like means along portions of the sidewall of the container, the flow control means having a recessed region formed in sidewall portions thereof to provide an annular space adjacent the upper surface of the gel-like means between proximal portions of the flow control element and the container. The flow control means is submerged to the extent that the upper surface of the gel-like means is positioned within the recessed region forming the annular space.

6 Claims, 8 Drawing Figures

APPARATUS FOR SEPARATING MULTIPHASE FLUIDS

BACKGROUND OF THE INVENTION

The present invention relates to apparatus for separating and partitioning differing-density phases of multiphase fluids, and more particularly to apparatus for separating and partitioning multiphase fluids which utilize gel-like material for partitioning the differing-density phases of such fluids.

The present invention is described in connection with and contemplates an improvement over the multiphase fluid separating and partitioning apparatus shown in U.S. patent application Ser. No. 452,059, now U.S. Pat. No. 3,920,549, filed on Mar. 18, 1974 and assigned to the assignee of the present invention. The apparatus described therein includes a container having an open end and a closed end, gel-like material initially positioned within the container adjacent the closed end, and energizer or flow control means initially partially submerged in the gel-like material for maintaining the gel-like material in its initial position prior to centrifugation and for influencing the gel-like material to flow, under the influence of centrifugal force, along wall portions of the container. The gel-like material is preferably thixotropic and has a density between the densities of the fluid phases to be separated; and the energizer or flow control means employed therein has a density greater than the density of the gel-like material.

The flow control means heretofore used in a blood separation apparatus is shown in FIG. 1. The container 2 is cylindrical in form, having a preferably permanently closed end 3 and an open end 4 provided with a stopper or closure 5. Gel-like material 6 is positioned within the container adjacent one end such as closed end 3. The flow control means 10a, is generally test-tube shaped and includes longitudinally extending equally spaced-apart ribs 11 on its cylindrical sidewall portion. Flow control means 10a is positioned within the gel-like material 6 by suitable means such as directly pushing the flow control means into the gel with a rod or stick. However, this method of seating the flow control means often results in the positioning of sidewall portions of the flow control means substantially adjacent wall portions of the container. That is, as shown in FIG. 1, the flow control means 10a may be positioned off-center or off-axis relative to the longitudinal axis of the container, such that a portion of one of the ribs 11 is separated from the adjacent or proximal portion of the wall of the container 2 only by a thin layer or column of gel-like material 6.

As is further shown by the enlarged sectional view in FIG. 1a, the close positioning of the energizer or flow control member of the conventional type relative to wall portions of the container establishes a capillary column whereby surface tension forces or capillary action cause the gel-like material at the surface level of the column to separate into a grease or thixotropic mixture portion 6 and an oil or liquid portion 6a. The separation of oil portion 6a from thixotropic portion 6 is hereinafter referred to as bleeding. Specifically, when the gel-like material is a thixotropic mixture of silicone oil and an inert siliceous filler, the capillary forces acting on that portion of the gel-like material 6 within the capillary column between the flow control means 10a and container wall 2 sometimes causes a silicone oil portion of the thixotropic gel-like material to bleed from the mixture.

The bleeding of oil or liquid from the gel-like material is a substantial problem because the oil may mix with the fluid to be separated and thus affect the quality of the subsequently separated phases. The oil or liquid used to make the gel-like material employed in a blood separation apparatus normally has a specific gravity lighter than the serum phase of blood; therefore, if the oil bleeds from the gel-like material, it could form a layer or float on top of the serum, or other lighter phase of blood, upon the completion of centrifugation. The layer of oil may also significantly affect the chemistries of the serum which are analyzed under current practice and also may contaminate the associated analytical apparatus, and therefore must be removed before such analysis.

The present invention has overcome the problem of bleeding of the oil or liquid portion from the gel-like material by providing an improved flow control means for use with such gel-like material.

SUMMARY OF THE INVENTION

The present invention is directed to an improved apparatus for collecting multiphase fluid such as blood and for separating and partitioning at least two differing-density phases of the fluid. The apparatus includes a cylindrical tubular container having a preferably permanently closed end and an open end; gel-like material, having a density intermediate the densities of the two phases, provided within the container adjacent the closed end; and an improved flow control or energizer element, symmetrical about an axis therethrough, comprising a bottom portion submerged within the gel-like material, and an top portion extending upwardly from the bottom portion having an annular radially recessed region formed therein which registers with the upper surface of the gel-like material, the flow control element having a density greater than the density of the gel-like material and having top plan dimensions such that gel-like material is permitted to flow between portions of the flow control element and wall portions of the container.

The improved flow control element is preferably provided with an axial cavity of sufficient size to make the flow control element float in the gel-like material at a depth such that the annular recessed region formed in the top portion provides a substantial annular space at the surface level of the gel-like material between sidewall portions of the flow control element and proximal portions of the container wall, such space being sufficiently large to prevent capillary forces from separating an oil or liquid portion from the surface portion of gel-like material within the annular space.

In one embodiment of the flow control element, the bottom portion is partially spherical in shape and terminates at a circular upper edge forming the maximum diameter of the element. An annular band or surface extends radially inwardly from the vicinity of the upper edge of the bottom portion. The top portion is cylindrical and is radially-inwardly off-set or recessed with respect to the circular upper edge and extends upwardly from an inner circumference of the annular band. An axial cavity is formed in an uppermost surface of the top portion. The flow control element is submerged within the gel-like material to below the height of the circular upper edge of the bottom portion and, due to the cavity, is buoyant within the gel-like material. Even if longitudinally aligned portions of the uppermost end of the top portion and the upper edge of the bottom portion abutt against the wall of the container, due to the off-set or recessed top portion, there will still be a substantial annular space at the upper surface level of the gel-like material interposed between the proximal portions of the container and flow control element.

In another embodiment, the top portion of the flow control element includes a frustoconical section extending inwardly and upwardly from an upper circular edge of the bottom portion forming a recessed portion above such edge, and a collar or flange section extending radially outwardly from the small upper end of the frustoconical section. Again, an axial cavity is formed in the top portion to assure that the member will float within the gel-like material. If longitudinally aligned portions of the flange section and upper edge of the bottom portion both abutt the sidewall of the container, the recessed portion will advantageously form a substantial annular space between the frustoconical section and the container wall at the upper surface of the gel-like material, thereby preventing capillary forces from acting upon the surface portion of the gel-like material within the thus-confined annular space to separate an oil or liquid portion therefrom.

DESCRIPTION OF THE PREFERRED EMBODIMENTS

Figure 1:
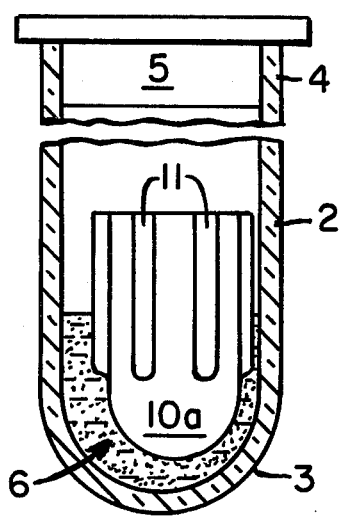
FIG. 1 is an elevational view partially in section of a conventional or prior art multiphase fluid separation apparatus which utilizes gel-like material as a partitioning medium.
Figure 1A:
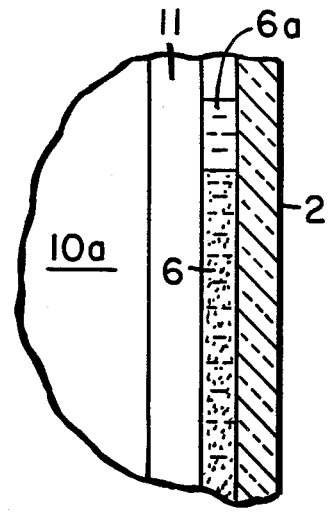
FIG. 1a is an enlarged fragmental view partially in section of a portion of the apparatus depicted in FIG. 1, showing a capillary-sized column or passageway formed between proximal portions of the prior art flow control or energizer means and the container wall.
Figure 2:
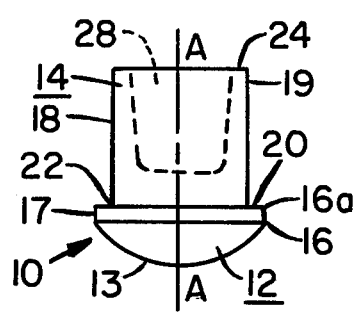
FIG. 2 is an elevational view of one preferred embodiment of an improved flow control element of the present invention.
Figure 3:
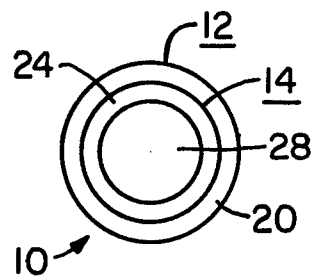
FIG. 3 is a top plan view of the flow control element illustrated in FIG. 2.
Figure 4:
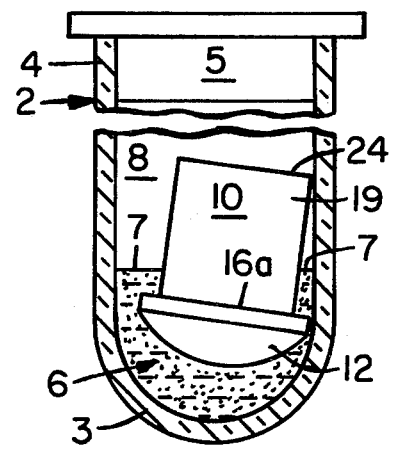
FIG. 4 is an elevational view partially in section of an improved multiphase fluid separating and partitioning apparatus incorporating the flow control element shown in FIGS. 2 and 3.

Referring now to the drawings, and particularly FIGS. 2, 3 and 4, a preferred embodiment of a flow control device or element 10 of the present invention is shown being provided with a bottom portion 12 and a top portion 14, both of which are symmetrical about an axis A—A through element 10. Bottom portion 12 preferably has a partially spherical lower face 13 which terminates at a circular upper edge 16. In order to facilitate the manufacture of the element 10, bottom portion 12 may include a short section 17, which is cylindrical in form, extending upwardly from edge 16 and terminating at a complementary circular upper edge 16a.

Top portion 14 is joined to bottom portion 12 within a plane formed by circular upper edge 16a, which may lie normal to axis A—A. Top portion 14 is recessed or radially-inwardly off-set from upper edge 16a by a distance equal to the width of an annular band or surface 20 lying in the plane of edge 16a. Annular band 20 has an inner circumference 22 at the juncture between it and top portion 14, and an outer circumference defined by upper edge 16a. Top portion 14 preferably has a cylindrical sidewall or lateral face 18 defined at its lower end by inner circumference 22 and at its upper end by an upper surface 24, preferably lying in a plane normal to axis A—A.

As illustrated in FIG. 4, flow control element 10 is employed in combination with a cylindrical tubular container or test tube 2 having a predetermined quantity of gel-like material 6 provided within the bottom closed end 3 of the test tube. Gel-like material 6 has a specific gravity or density which is less than the specific gravity or density of the heavier phase of the fluid to be separated but greater than the specific gravity or density of the lighter phase to be separated. Flow control element 10 has a specific gravity or density greater than that of the gel-like material, such that, during centrifugation, the flow control element 10 influences gel-like material to flow between portions of its periphery and portions of the inner surface of tube 2. Accordingly, the maximum diameter of element 10 as represented by edges 16 and 16a, is less than the inner diameter of container or tube 2, such that gel-like material is permitted to flow upwardly between element 10 and the wall of tube 2. The bottom face 13 is preferably adapted to mate with or at least complement a portion of the closed end 3 of container 2, thereby directing as much gel-like material as possible from its initial tube-bottom position.

It should be noted that container 2 may have normally open top and bottom ends, with each being sealed by a suitable stopper or closure. Accordingly, the term, "closed end," is used herein to denote that end portion of the tube into which the gel-like material is initially deposited, and which also is positioned within a centrifuge, or assumes a position during centrifugation, farthest away from the axis of rotation of the centrifuge. The closed end of the container thus may be permanently closed and generally semi-spherical in form, or it may be formed by the combination of a closure and the sidewall of the container and may have a complex shape. When the latter type of container is employed, it is desirable to utilize a flow control element having a bottom portion provided with a lower face designed to complement or mate with an inner surface portion of the closure within the closed end of the container.

An axial cavity 28 extending downwardly into top portion size and shape of axial cavity 28 is adapted to make the flow control element float within gel-like material 6, thereby eliminating any concern that, during shipment, storage or handling, it may submerge below the upper surface of the gel-like material. Also, the size of cavity 28 is preferably large enough to assure that the flow control element will reach a point of neutral bouyancy at a depth great enough to assure that the upper edge 16a of bottom portion 12 is completely submerged below the upper surface 7 of gel-like material 6.

As shown in FIG. 4, the flow control element 10 may be positioned off-center or off-axis such that longitudinally aligned portions of bottom portion upper edge 16a and of upper end 19 of top portion 14 may contact the same side of the sidewall of container 2, with the element being submerged such that the upper surface 7 of the gel-like material 6 is above upper edge 16a. It will be appreciated that an annular radially recessed region is formed by the adjoining surfaces of annular band 20 and cylindrical lateral face 18 due to the fact that the top portion 14 is recessed from upper edge 16a. The radially recessed region provides a substantial annular space between the element 10 and container 2, especially between proximal wall portions of the container and flow control element vertically interposed between the aforementioned abutting, longitudinally aligned portions. Accordingly, by virtue of the radially recessed region, the surface portion of the gel-like material 6 lying between such proximal container and flow control element portions is not subjected to capillary forces of a magnitude sufficient to cause bleeding of liquid from the gel-like material. For example, when the gel-like material consists essentially of a thixotropic mixture of a silicone oil and a finely divided siliceous filler, the recessed region provides sufficient space so that there is no need for concern about the bleeding of the oil from the mixture due to capillary action within such annular space between the element 10 and container 2.

Preferably, cavity 28 is frustoconical and extends only partially through the top portion 14, thereby forming a hollowed flow control element which is heavier at its bottom than its top. The shape and weight distribution of the thus-formed flow control element is suitable for angle-head or swinging-basket centrifuges, because the centrifugal force exerted on element 10 causes its axis A—A to generally align itself with the axis of tube 2. The self-alignment of the energizer tends to more evenly distribute the gel-like material about the periphery thereof.

Figure 6:
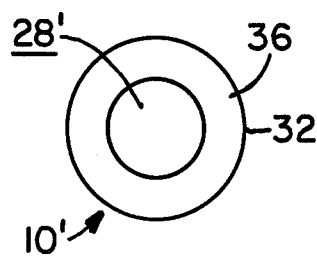
FIG. 6 is a top plan view of the flow control element illustrated in FIG. 5.
Figure 7:
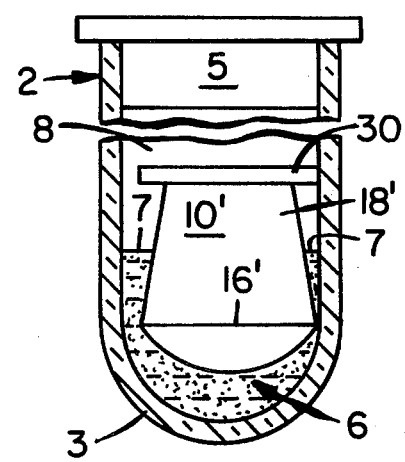
FIG. 7 is an elevational view partially in section of an improved blood separating and partitioning assembly utilizing the flow control element shown in FIGS. 5 and 6.

In another preferred embodiment of the improved multiphase fluid separation apparatus of the present invention, as shown in FIGS. 6 through 8, the flow control element 10' includes a partially spherical bottom portion 12', having a circular upper edge 16', and a top portion 14' having an upwardly and inwardly tapering frustoconical section or lateral face 18' adjoining bottom portion 12' at circular edge 16', and a collar portion 30 extending radially outwardly from frustoconical face 18' at the upper end 19' thereof. Collar 30 is preferably circular in top plan view, having respective upper and lower annular faces, 36 and 34, respectively, defined at their outer circumference by a lateral face 32. The diameter or overall width of collar 30 is substantially greater than the outer diameter of the small end 19' of frustoconical section 18' providing a recessed portion along section 18', and is preferably equal to the diameter of the circular upper edge 16' of bottom portion 12'. The maximum outer diameter or top plan dimensions of element 10', as represented by the diameters of upper edge 16' and lateral face 18', are sufficiently smaller than the inner diameter of tube 2 to provide for movement of gel-like material 6 between portions of element 10' and tube 2 or, vice versa, movement of the element 10' through gel-like material 6. A cavity 28' is formed in the upper surface 36 of element 10' for the same reasons as mentioned above regarding cavity 28.

The flow control element 10' may be pushed into gel-like material 6 such that, at a side of the inner surface container 2, portions of collar 30 and upper edge 16' are contacting or abutting the container inner wall at points lying generally in a straight line parallel to the axis of tube 2. The upper edge 16' is submerged below the surface 7 of gel-like material 6, and due to the recessed region formed by the inwardly tapering surface 18' in conjunction with collar 30, disposed between the element 10' and tube 2.

The flow control element is made from a material chosen primarily according to its specific gravity or density, which as mentioned above must be greater than the density of the gel-like material 6. When incorporated in an apparatus for separating and partitioning blood, it is preferable that the flow control element have a density substantially greater than that of the gel-like material to assure reasonably rapid movement of the gel from its initial tube-bottom position. Also, when used in blood separation apparatus, the material should be inert or noninteractive with the constituents of the blood, so as not to affect the values or quantities of such constituents to be subsequently measured by customary analytical techniques. Preferably, the material is a plastic or synthetic resin, such as a clear acrylic plastic.

The following specific example of a blood collection and separation apparatus is given by way of illustration and is not intended to limit of the present invention to any specific shapes, dimensions or materials. Container 2 was a standard 10 ml. glass test tube obtainable from Corning Glass Works having a generally spherical closed bottom end 3 and having an inner diameter of approximately 0.550 inch. Approximately 1.85 grams of gel-like material 6 consisting essentially of a thixotropic mixture of silicone oil and finely divided silica and having a specific gravity of 1.042 was deposited at the closed end 3 of the tube. The gel-like material had a density adapted to reach a point of neutral bouyancy or equilibrium between separated serum and clotted red cell phases.

Figure 5:
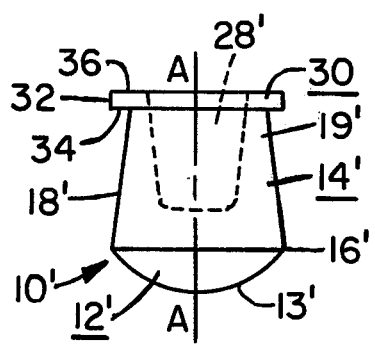
FIG. 5 is an elevational view of another preferred embodiment of the improved flow control element of the present invention.

The flow control element 10, as shown in FIGS. 3 through 5, had a spherical bottom end 14 having a radius of approximately 0.375 in., a maximum diameter of 0.510 in. at the upper edge 16 of bottom portion 12, and an cylindrically-shaped top portion 14 having a height of approximately 0.55 in. and an outer diameter of 0.457 in. Cavity 28 was frustoconical in form, had an inner major diameter of 0.413 in., and had a generally flat bottom surface lying 0.10 in. above the plane through annular upper surface 20. Element 10 was made from a clear, virgin acrylic plastic obtainable from DuPont de Nemours, E. I. and Co. and sold under the tradename, "Lucite 14, NC-10"; it had a specific gravity of approximately 1.20.

Flow control element 10 was pushed into a partially submerged position within gel-like material 6 to the extent that bottom portion 12 was completely below the upper surface 7 of the gel-like material. Then, the tube was substantially evacuated; and a needle puncturable stopper or closure 5 was pressed into an airtight sealing relationship with the upper end 4 of the tube, thus forming a fluid or blood receiving chamber 8. The recessed region of the flow control element 10, formed by the off-set top portion 14, provided sufficient annular space between wall portions of the element and the tube 2 at the surface of the gel-like material to prevent detrimental capillary action therebetween and thereby inhibit the bleeding of oil from the gel mixture. In this configuration, the assembly was ready for siphoning blood into chamber 8 by the customary venipuncture technique, which uses a double-ended needle device, as is well-known to those skilled in the art.

After blood was siphoned into the chamber 8, the stoppered and filled tube was centrifuged to separate the blood into a lighter serum phase and a heavier cellular or clotted red cell phase. During centrifugation, flow control element was forced by the centrifugal force toward tube bottom end 3, thereby initiating and influencing the gel-like material 6 to flow upwardly along wall portions of the tube between lateral or peripheral portions of element 10 and side wall portions of tube 2. Due to its intermediate density, the gel-like material reached a level of equilibrium between the lighter and heavier phases and formed a transversely continuous partitioning means between the fully separated phases.

The stopper 5 was thereafter removed when it was desired to remove the lighter phase from above the thus-formed partitioning means. Advantageously, there was no concern about the presence of a film of oil, separated from the gel-like material 6, floating on the surface of the lighter phase and, accordingly, no need to aspirate off such an oily film. The lighter phase was simply decanted from above the gel-like partitioning means.

While this invention has been described in connection with possible forms or embodiments thereof, it is to be understood that changes or modifications may be resorted to without departing from the spirit of the invention or scope of the claims which follow.

What is claimed is:

1. An improved apparatus for separating and partitioning different density phases of a multiphase fluid such as blood comprising, a tubular container having a closed end, inert thixotropic gel-like means having a density intermediate the density of said fluid phases initially positioned adjacent said closed end for separating said phases upon centrifugation, said gel-like means including a mixture of an oil and a filler and flow control means having a density greater than the density of said gel-like means initially partially submerged within a surface portion of said gel-like means for directing the flow thereof during centrifugation along wall portions of said container, wherein the improvement comprises: said flow control means including a bottom portion and a top portion extending upwardly from said bottom portion, and said top portion having an annular recessed region formed therein such that said recessed region provides an annular space between wall portions of said top portion and said container adjacent the surface of said gel-like means.

2. An improved apparatus for collecting a multiple phase fluid such as blood and for separating and partitioning said fluid into a lighter phase and a heavier phase of the type comprising a tubular container, thixotropic gel-like material initially positioned adjacent a closed end of said container, with said gel-like material being chemically inert to said phases, having a density intermediate the density of said phases, and including therein a mixture of an oil and a filler, and a flow control element initially partially submerged in said gel-like material and arranged for influencing said gel-like material to flow during centrifugation along wall portions of said container, said flow control element having a density greater than the density of said gel-like material, wherein the improvement comprises: said flow control element including a bottom portion and a top portion extending from said bottom portion; said top portion having an annular radially recessed region formed transversely therein; and, said flow control element being partially submerged bottom portion first into said gel-like material to the extent that the upper surface of said gel-like material registers with said recessed region.

3. The improved apparatus of claim 2 wherein said flow control element includes an axial cavity formed therein of a volume sufficient to make said flow control element float within said gel-like material at a depth such that the upper surface of said gel-like material remains in a registered relationship with said radially recessed region.

4. The improved apparatus of claim 2 wherein said flow control element is symmetrical about an axis and includes a bottom portion of a generally partially spherical shape terminating in an upper circular edge, and an annular band extending radially inwardly from the vicinity of said bottom portion upper edge and a cylindrical lateral face extending upwardly from an inner circumference of said annular band, with said cylindrical lateral face and said annular band defining said radially recessed region.

5. The improved apparatus of claim 2 wherein said flow control element is symmetrical about an axis and includes a bottom portion having a circular upper edge, and a top portion having an upwardly and inwardly tapering frustoconical lateral face extending upwardly from said circular edge and a collar section having a lower face extending radially outwardly from the upper end of the frustoconical section, said collar lower face and said frustoconical lateral face defining said radially recessed region.

6. An improved apparatus for collecting a multiple phase fluid such as blood and for separating and partitioning said fluid into a lighter phase and a heavier phase of the type comprising a tubular container, thixotropic gel-like material initially positioned adjacent a closed end of said container, with said gel-like material being chemically inert to said phases, having a density intermediate the density of said phases, and including therein a mixture of an oil and a filler, and a flow control element initially partially submerged in said gel-like material and arranged for influencing said gel-like material to flow during centrifugation along wall portions of said container, said density of said gel-like material, wherein the improvement comprises: said flow control element having a bottom portion terminating in an upper edge; a top portion communicating with said bottom portion in the plane formed by said upper edge; and said top portion being radially-inwardly offset with respect to said upper edge to form a recessed region above said upper edge such that an annular space is formed between wall portions of said top portion and said container when said flow control element is partially submerged within said gel-like material.

* * * * *

UNITED STATES PATENT AND TRADEMARK OFFICE
CERTIFICATE OF CORRECTION

PATENT NO. : 3,981,804

DATED : September 21, 1976

INVENTOR(S) : Joseph F. Gigliello

It is certified that error appears in the above—identified patent and that said Letters Patent are hereby corrected as shown below:

Column 8, line 55, after second occurrence of "said", insert -- flow control element having a density greater than the -- .

Signed and Sealed this

Fourth Day of January 1977

[SEAL]

Attest:

RUTH C. MASON
*Attesting Officer*

C. MARSHALL DANN
*Commissioner of Patents and Trademarks*